United States Patent [19]
Avila

[11] 3,986,504
[45] Oct. 19, 1976

[54] INTERNAL FIXATION DEVICE FOR SECURING TWO FRACTURED BONE JOINTS TOGETHER

[76] Inventor: Rafael Pares Avila, 352 Napoles St., Barcelona, Spain

[22] Filed: Oct. 28, 1975

[21] Appl. No.: 626,327

[30] Foreign Application Priority Data
Oct. 25, 1974  Spain .................................. 207117

[52] U.S. Cl. ........................................... 128/92 BC
[51] Int. Cl.$^2$ ............................................. A61F 5/04
[58] Field of Search ............ 128/92 B, 92 BC, 92 R, 128/92 D, 92 G, 83

[56] References Cited
UNITED STATES PATENTS

| | | | |
|---|---|---|---|
| 2,998,007 | 8/1961 | Herzog ............................ | 128/92 BC |
| 3,680,553 | 8/1972 | Seppo ............................. | 128/92 BC |
| 3,760,802 | 9/1973 | Fischer et al. .................. | 128/92 BC |

FOREIGN PATENTS OR APPLICATIONS

| | | | |
|---|---|---|---|
| 2,224,214 | 11/1973 | Germany ......................... | 129/92 BC |
| 453,570 | 6/1968 | Switzerland .................... | 128/92 BC |

*Primary Examiner*—John D. Yasko
*Attorney, Agent, or Firm*—McGlew and Tuttle

[57] ABSTRACT

An internal fixation device for securing two adjacent fractures bone parts together comprises a tubular member which is adapted to be driven into the two fractured bone parts. The tubular member has a plurality of circumferentially arranged and longitudinally extending slots therein at two longitudinally spaced locations which would normally be aligned with the respective bone joints. A shaft member is engaged in the tubular member and has a threaded portion in the vicinity of each set of slots. A nut member is engaged on the threaded portion adjacent each slot and has a fin part which extends through the slot and is engageable with the bone part. To facilitate the outward movement of the fins which are carried on a cylindrical bushing so as to extend axially outwardly from one end a spring is positioned around the rod and a cam member in the form of a cylindrical bushing is disposed between each end of the spring and an associated internally threaded bushing which carries the fins. When the bushings are displaced along the threaded portions the cam member contacts the fins and pushes them radially outwardly through the slot to engage into the associated bone joint structure. The bushings are advanced along the rod member by rotating the rod member which preferably has threads arranged so that the bushings move in directions toward each other to advance the bone joint parts together and to close the joint therebetween.

4 Claims, 4 Drawing Figures

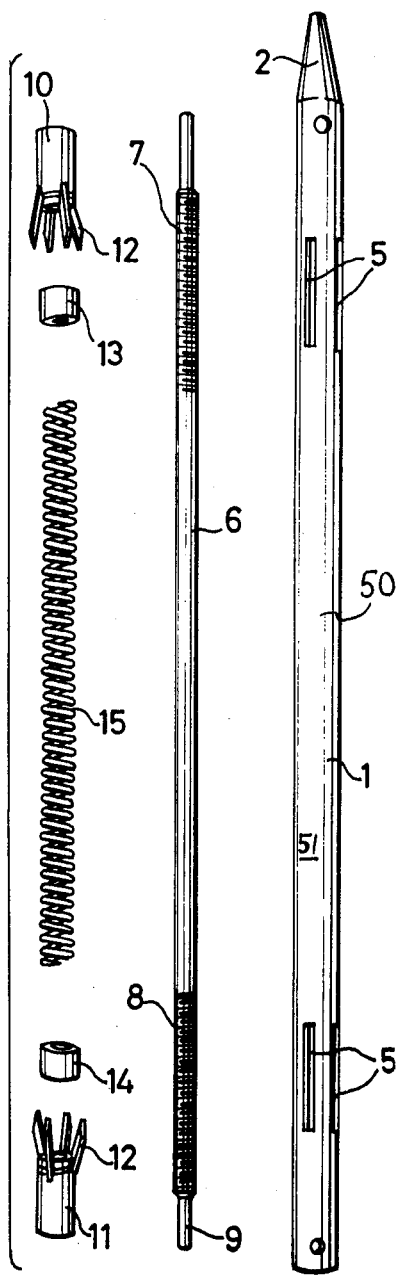
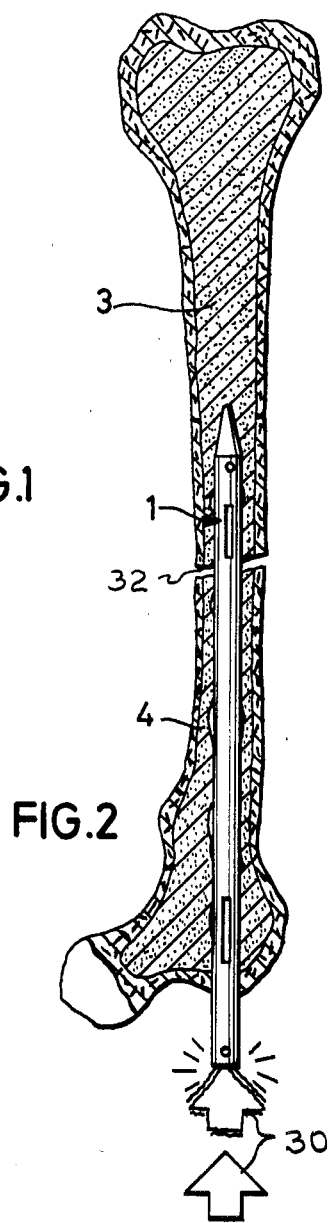
FIG.7  FIG.6  FIG.1  FIG.2

INTERNAL FIXATION DEVICE FOR SECURING TWO FRACTURED BONE JOINTS TOGETHER

BACKGROUND OF THE INVENTION

1. Field of the Invention

This invention relates in general to surgical devices for fixing broken bone parts and in particular to a new and useful internal fixation device for securing two adjacent fractures bone parts together.

2. Description of the Prior Art

At the present time many types of devices are known for securing bone joints together so that the fractures will heal in a satisfactory manner. In one known device the separated bone joint parts on each side of the fracture are clamped by devices which must be secured completely around their circumference and they are pulled together in order to position them as close as possible to effect a healing between the separated bone parts. Other types of devices for securing the bone parts in position include tensioning members and fixing nails which are inserted in order to affect the required compression of the bone parts in order to position them in a satisfactory position for healing.

SUMMARY OF THE INVENTION

The present invention provides a device which includes a tubular member which is driven through the two bone parts first entirely through one and then into the other. The member carries a shaft member therein which includes a threaded area adjacent each end which underlies a longitudinally elongated slot or slots defined in the outside tubular member. Preferably a spring is disposed between two nut members which are rotatably engaged on respective threaded portions of the shaft in order to urge a camming member in a direction toward the nut member so that when it is rotated relative to the threaded portion of the shaft member it will engage a camming member disposed between the spring and the nut member to force fins carried by the nut member outwardly through the slots into engagement with the bone material of the associated bone joint. Thus after the tubular member is inserted the rod is rotated to cause respective spaced apart nut members to position the fins carried thereby into engagement with the associated bone joint and to migrate along the shaft member with the associated bone joint in a direction to close the spacing between the bone fragments.

Accordingly it is an object of the invention to provide a bone implant device for facilitating the fixation of two bone parts on each side of a bone fracture which includes a tubular member which is adapted to be driven through the bone parts and which carries the nut member which is advanced so as to engage each associated bone part to move it in opposite directions to close the bone joint.

A further object of the invention is to provide an internal fixation device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there are illustrated preferred embodiments of the invention.

BRIEF DESCRIPTION OF THE DRAWINGS

IN THE DRAWINGS

Figures 3, 4, 5:
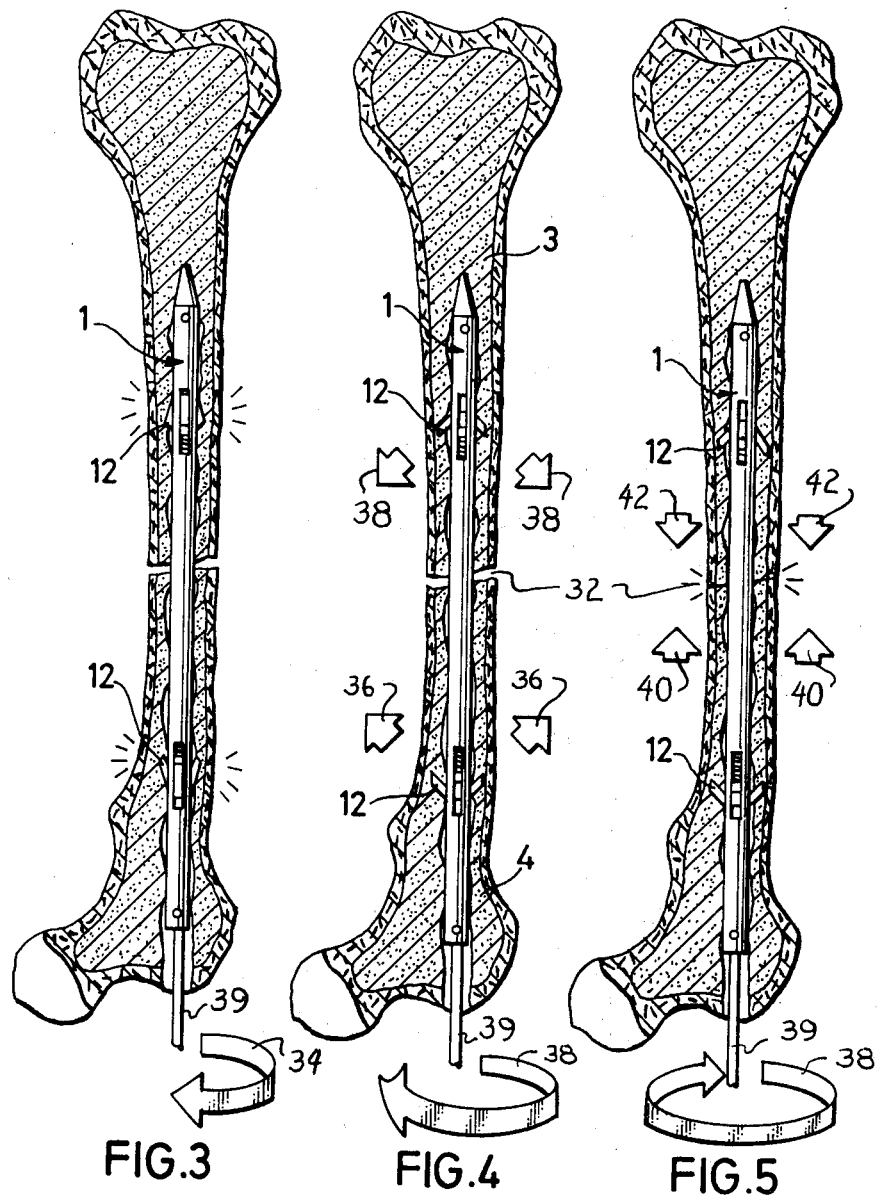

FIG. 1 is a side elevational view of an internal fixation device constructed in accordance with the invention;

FIG. 2 is a cross-sectional view of a fractured leg bone having an internal fixation device extending through two of the leg bone joints on each side of a fracture;

FIGS. 3, 4 and 5 show views similar to FIG. 2 in various stages of operation of the device;

FIG. 6 is a side elevational view of a shaft member used with the fixation device; and FIG. 7 is an exploded perspective view of various operating parts which fit over the shaft member shown in FIG. 6.

GENERAL DESCRIPTION OF THE PREFERRED EMBODIMENT

Referring to the drawings in particular the invention embodied therein comprises a fixation device or assembly generally designated 1 which comprises an elongated tubular member 50 having a shank portion 51 and a pointed end portion 2. The shank portion 51 is provided with a plurality of longitudinally elongated and circumferentially arranged slots 5 which provide openings for the passage of bone engagement members or fins 12 which are carried on nut members 10. The nut members 10 are threadably engageable on longitudinally spaced threaded portions 7 and 8 of a shaft member 6 which is positioned within the tubular member 1 so that the threaded portions 7 and 8 are disposed in the vicinity of the slots 5. An elongated compression spring 15 is fitted over the central smooth portion of the shaft member 6 along with ring or cam member 13 and 14 at the respective ends thereof. When the nut member 10 is rotated relatively to the shaft member 6 in a direction such that it moves axially inwardly it will contact first the ring member 13 which is held against axial displacement by the spring 15 so that the engagement fins 12 are moved by the ring member 13 outwardly through the slot 5 and become embedded into the material of the bone joint either 3 or the bone joint 4 in accordance with which nut member 10 or 11 is engaged therewith. In the preferred operating position both nut members 10 and 11 are arranged to underlie the slots 5 at the respective ends of the tubular member 1 and when the shaft member 6 is rotated the nut members 10 and 11 move together inwardly toward each other so as to cause the respective engagement fins 12 to penetrate through a respective slot and into an associated bone fragment 3 or 4. To facilitate rotation of the shaft member 6 it is provided with a smooth or stem portion 9 which may be engaged and driven from the exterior of the tubular member 2 with a tool 39 to effect the desired rotation. It would also be possible to arrange the threaded portion so that the nut members 10 and 11 move either in directions toward each other, or away from each other, or, if desired, separately in the same direction for some special bone fixation or separation purposes.

The normal operation of the device includes an insertion of the whole assembly 1 including the tubular member 50, the rod member 6 and the associated parts 10, 11, 12, 13, 14 and 15. The complete fixation device is inserted preferably into the bone by hammering in the direction of the arrow 30 to drive the complete fixation device completely through at least one of the bone joints such as the bone joint 4 and into the next bone joint which lies on the other side of a fracture line 32.

With the parts 6 to 15 already within the tubular member 50 it is possible to begin engagement of the bone particles for example with the tubular member 50 and the assembly of parts positioned as indicated in FIG. 3. This is done by rotating the end portion 9 of the shaft member 6 in a direction of rotation 34 which advantageously is one in which both nut members 10 and 11 are moved along the shaft member 6 with the tool 39 toward each other. When they have been moved sufficiently the ring member 13 and 14 would cause an outward spreading of the engagement fins 12 to cause them to move through the associated slots 5 and into engagement with the respective bone joint 3 or 4. This outward penetrating interengagement of the fin members 12 with the bone materials are indicated by arrows 36, 36 and 38, 38. Upon further rotation in the direction of arrow 38 there is a further migration of the nut members 10 and 11 with the associated fin members 12 to cause the bone fragments 3 and 4 to be moved along with it and in a direction to close the fractured joint 32 as indicated by arrows 40, 40 and 42, 42. Finally, the outside tool 39 coupled to the end portion 9 is removed.

While a specific embodiment of the invention has been shown and described in detail to illustrate the application of the principles of the invention, it will be understood that the invention may be embodied otherwise without departing from such principles.

What is claimed is:

1. An internal fixation device for securing two adjacent fractured bone joints together, comprising a tubular member adapted to be driven into the two fractured bone parts and having at least one slot at two longitudinally spaced apart locations each adaped to align with a respective bone part, a shaft member engaged in the tubular member and having a threaded portion in the vicinity of each slot, a nut member engaged with each threaded portion, a fin part carried by said nut member and engageable through the adjacent slot into the associated bone joint, said shaft member and said nut member being relatively rotatable to advance said nut members along the respective threaded portions and to cause said fin part to move outwardly into engagement with the associated bone joint and to move said bone joint along therewith.

2. An internal fixation device according to claim 1, wherein said nut member comprises a cylindrical bushing having an interior threading, said fin parts comprising at least one fin extending from the associated nut member in the direction toward the other nut member, spring means around said shaft member and a cam member disposed between said spring means and each associated nut member engageable with said fin part to urge it to outwardly upon movement of said nut member along said shaft member.

3. An internal fixation device according to claim 1, wherein said shaft member comprises a rod having at least one end extending beyond the threaded end but not projecting out of said tubular member, said end being engageable for rotating said rod from the outside with a suitable tool.

4. An internal fixation device according to claim 3, including a compression spring over said shaft member, a cylindrical cam member at each end of said compression spring, said nut member comprising a cylindrical member having a plurality of fins hinged thereto at spaced locations around the circumference thereof and extending rearwardly toward said cam member, said threaded portion of said shaft being such that said nut member is advanced inwardly along said shaft member whereby both of the engaged bone parts are pulled together.

* * * * *